(12) United States Patent
Bartelmuss

(10) Patent No.: US 10,466,192 B2
(45) Date of Patent: Nov. 5, 2019

(54) METHOD AND APPARATUS FOR MEASURING THE MOISTURE CONTENT OF PULP MATERIAL ON A WIRE

(71) Applicant: Klaus Bartelmuss, Teufenbach (AT)

(72) Inventor: Klaus Bartelmuss, Teufenbach (AT)

( * ) Notice: Subject to any disclaimer, the term of this patent is extended or adjusted under 35 U.S.C. 154(b) by 419 days.

(21) Appl. No.: 15/449,429

(22) Filed: Mar. 3, 2017

(65) Prior Publication Data

US 2017/0307555 A1 Oct. 26, 2017

(30) Foreign Application Priority Data

Apr. 25, 2016 (AT) .................. A 211/2016

(51) Int. Cl.
| | | |
|---|---|---|
| *G01N 27/04* | (2006.01) | |
| *G01N 33/34* | (2006.01) | |
| *G08B 5/36* | (2006.01) | |
| *D21F 7/00* | (2006.01) | |

(52) U.S. Cl.
CPC ........... *G01N 27/048* (2013.01); *D21F 7/003* (2013.01); *G01N 33/343* (2013.01); *G08B 5/36* (2013.01)

(58) Field of Classification Search
None
See application file for complete search history.

(56) References Cited

U.S. PATENT DOCUMENTS

| 3,253,315 A | * | 5/1966 | Eicken | .................. D06B 23/26 |
| | | | | 28/183 |
| 8,368,407 B2 | | 2/2013 | Cristini | |

FOREIGN PATENT DOCUMENTS

EP         2162731 B1      11/2014

* cited by examiner

*Primary Examiner* — Jermele M Hollington
*Assistant Examiner* — Suresh K Rajaputra
(74) *Attorney, Agent, or Firm* — Laurence A. Greenberg; Werner H. Stemer; Ralph E. Locher

(57) ABSTRACT

A method and apparatus for measuring the moisture content of pulp material on a wire in an installation for producing paper. The apparatus includes a measuring device for measuring the moisture content of the pulp material. The apparatus has a moisture sensor, a control and data processing unit assigned to the measuring device, and a transmitting and receiving device and/or a connection for a data line for transmitting the measured data to the control and data processing unit. The measuring device for measuring the moisture content of the pulp material includes a pressure measurement device for determining and displaying a pressure range with which it is being pressed against the wire. The contact pressure is controlled and taken into account during the measurement of the moisture content.

19 Claims, 4 Drawing Sheets

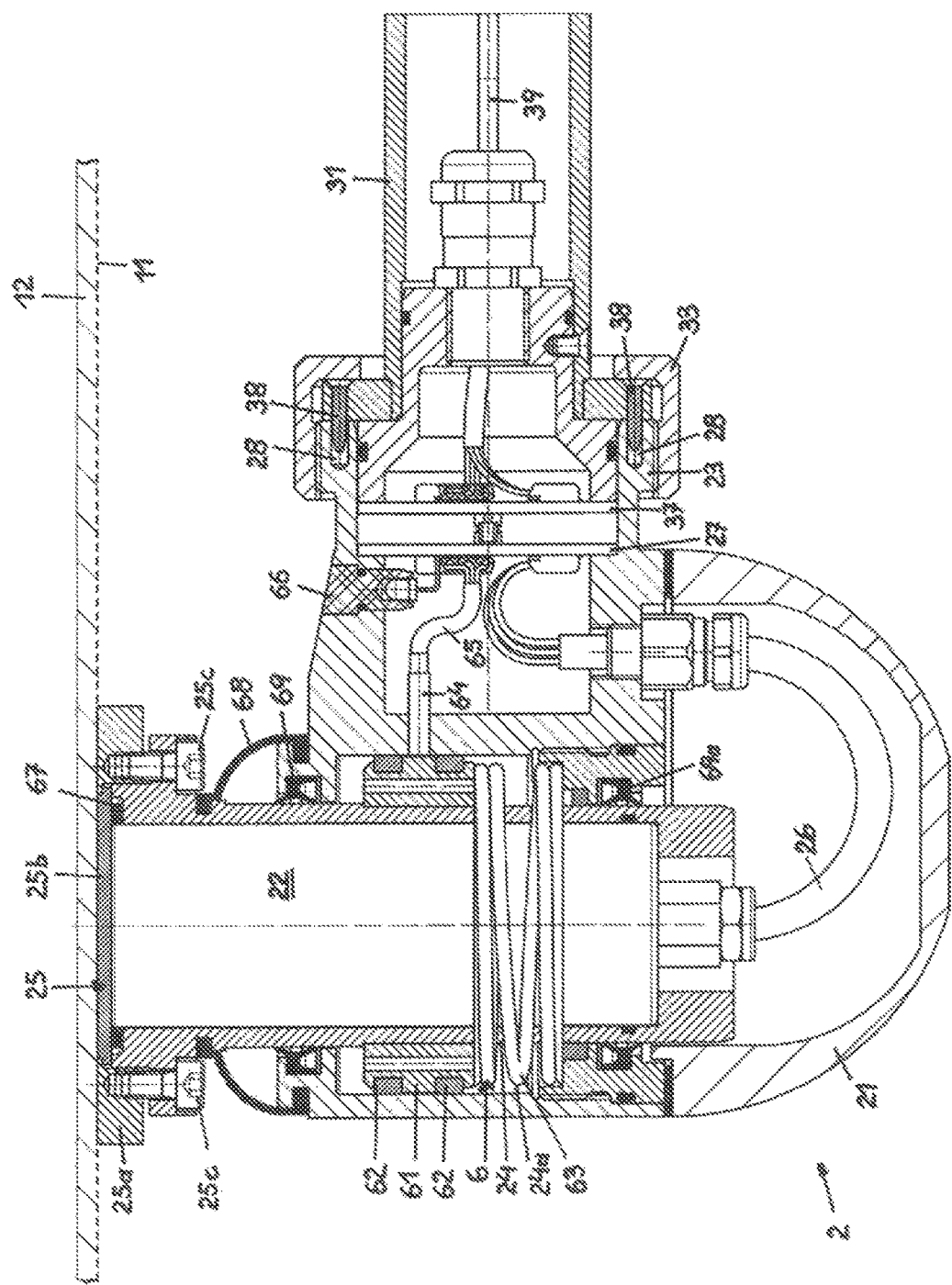

METHOD AND APPARATUS FOR MEASURING THE MOISTURE CONTENT OF PULP MATERIAL ON A WIRE

CROSS-REFERENCE TO RELATED APPLICATION

This application claims the priority, under 35 U.S.C. § 119, of Austrian patent application A 211/2016, filed Apr. 25, 2016; the prior application is herewith incorporated by reference in its entirety.

BACKGROUND OF THE INVENTION

Field of the Invention

The present invention relates to a method and an apparatus for measuring the moisture content of pulp material on a wire in a papermaking installation, having a means for measuring the moisture content of the pulp material, having a control and data processing unit assigned to the means, and having a transmitting and receiving device and/or having a connection for a data line for transmitting the measured data to the control and data processing unit.

In an installation for producing paper, it is known to measure the moisture content of the pulp material on the wire and to use the measured values determined in this way for controlling the operation of this installation. These measurements are performed at different points over the length of the wire and at a distance of about half a meter to one meter from one of the side edges of the wire. The values of the moisture content of pulp material that are determined at the individual measuring points are entered into a data memory.

For the performance of these measurements, use is made of measuring rods which, at one of the two ends thereof, are formed with a means for measuring the moisture content of the pulp material on the wire. In order to be able to perform the measurements, the measuring device is pressed onto the underside of the wire by means of the measuring rod at predefined measuring points.

With regard to this known prior art, reference is made, for example, to U.S. Pat. No. 8,368,407 B2 and its counterpart European patent No. EP 2162731 B1.

However, the requirement for optimal control of the drying process is not met by that known prior art since, during these measurements, the pressure with which the measuring device is pressed onto the wire is not taken into account.

SUMMARY OF THE INVENTION

It is accordingly an object of the invention to provide a method and an apparatus for measuring the moisture content of pulp material on a wire which overcome the above-mentioned and other disadvantages of the heretofore-known devices and methods of this general type.

With the foregoing and other objects in view there is provided, in accordance with the invention, a method for measuring a moisture content of pulp material on a wire in an installation for producing paper, the method comprising:

providing a measuring device for measuring the moisture content of the pulp material and a control and data processing unit configured to receive measured data from the measuring device;

measuring the moisture content of the pulp material with the measuring device and concomitantly pressing the measuring device onto an underside of the wire with a given contact pressure; and determining the contact pressure with which the measuring device is pressed onto the underside of the wire and measuring the moisture content while maintaining the contact pressure within a predefined range.

With the above and other objects in view there is also provided, in accordance with the invention, an apparatus for measuring the moisture content of pulp material on a wire in an installation for producing paper. The apparatus comprising:

a measuring device for measuring the moisture content of the pulp material and acquiring measured data, the measuring device including a moisture sensor and an optional attachment member for affixing to a measuring rod;

a control and data processing unit;

a transmitting and receiving device and/or a connection terminal for a data line for transmitting the measured data to the control and data processing unit; and the measuring device including a pressure measurement device for determining and displaying a pressure range with which the measuring device is pressed against the wire.

In other words, the objects of the invention are achieved in that, during the measurement of the moisture content, the pressure with which the means for measuring the moisture content is pressed onto the underside of the wire is determined, and the measurement of the moisture content is carried out in a predefined range of this contact pressure.

In an apparatus according to the invention, the means for measuring the moisture content of the pulp material is formed with a measuring device for determining and displaying that pressure range with which the means for measuring the moisture content of the pulp material is pressed against the wire.

The means for measuring the moisture content is preferably formed with a housing, in which a moisture sensor, which is subject to the action of a spring element, can be displaced. In particular, the housing is formed with a cylindrical cavity, in which the moisture sensor is located and in which it can be displaced under the action of the spring element. The spring element is preferably formed by a helical compression spring, which acts between the moisture sensor and the housing.

In this case, the cylindrical cavity in the housing can be formed with a region of annular cross section and the moisture sensor can be formed with a sliding sleeve fixed to the latter, which projects into the annular region and can be displaced between its end faces. In particular, the spring element is located between the sliding sleeve and the housing.

The moisture sensor is preferably formed, on its side facing the wire, with a wear-resistant support, in particular a plate made of a ceramic material, which is replaceably fixed to the moisture sensor. Furthermore, a seal can be provided between the support of ceramic material and the moisture sensor. In addition, the moisture sensor and the housing are preferably sealed off with respect to the entry of liquid by means of a resilient sealing cuff and, if appropriate, by means of at least one sealing ring.

Preferably, the sliding sleeve is assigned at least one position sensor, by means of which the position of the moisture sensor with respect to the housing is determined and displayed. For this purpose, the sliding sleeve can be formed with two sliding rings located at an axial distance from each other, which interact with the position sensor.

Furthermore, an LED lamp preferably located in the housing can be connected to the position sensor, by means of which a light signal is output as soon as the position sensor is located in the region between the sliding rings as a result of a displacement of the moisture sensor with respect to the housing.

The housing of the measuring device and the measuring rod are preferably formed with coupling parts assigned to one another for their mechanical and electrical connection. Here, the coupling parts are preferably formed with circuit boards assigned to each other and centering elements. In addition, the length of the measuring rod can be adjustable and fixable.

Other features which are considered as characteristic for the invention are set forth in the appended claims.

Although the invention is illustrated and described herein as embodied in a method and apparatus for measuring the moisture content of pulp material on a wire, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2, FIG. 2A, FIG. 2B, FIG. 2C show the individual constituent parts of the apparatus according to FIG. 1, in an axonometric illustration;

FIG. 3A is a similar section through the apparatus according to FIG. 3 in a second position of the device for determining the contact pressure.

DETAILED DESCRIPTION OF THE INVENTION

Figure 1:
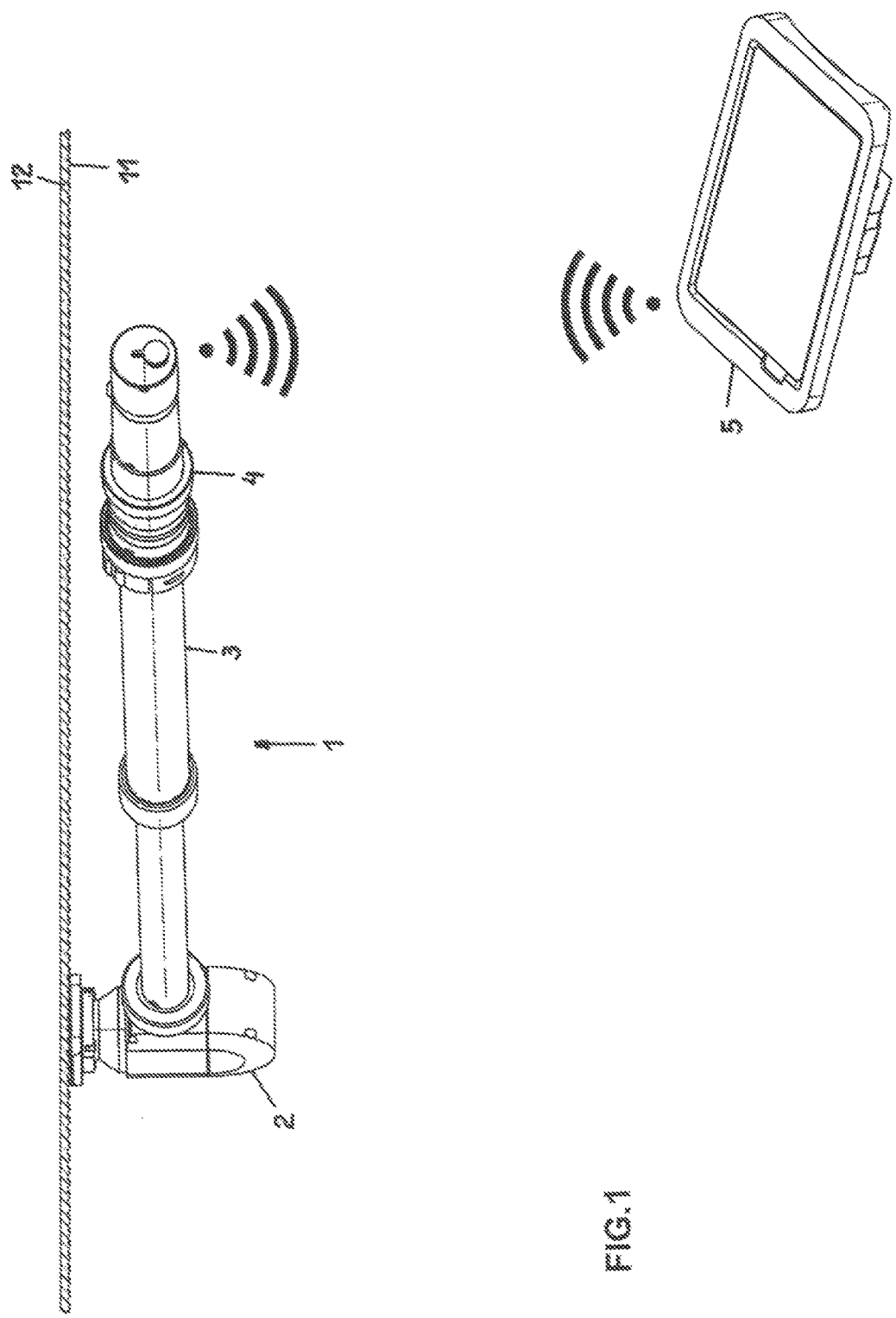
FIG. 1 shows an apparatus for measuring the moisture content of the pulp material on a wire in an installation for producing paper, in an axonometric illustration.

Referring now to the figures of the drawing in detail and first, particularly, to FIG. 1 thereof, there is shown an apparatus 1 for measuring the moisture content of pulp material 12 on a wire 11 in an installation for producing paper, i.e., a papermaking installation. The apparatus 1 has a measuring device 2, a measuring rod 3, a handle part 4 and a control and data processing unit 5.

In order to perform the measurements, the measuring device 2 is pressed by means of the measuring rod 3 against the underside of the wire 11, on the upper side of which the pulp material 12 is located. These measurements are performed at predefined points over the length of the wire 11 and at a distance of about half a meter to one meter from one of the edges of the wire 11. The length of the measuring rod 3 is adjustable and fixable. The necessary electric and electronic means for performing and controlling the measurements are located in the handle part 4. In particular, in the handle part 4 there is a transmitting and receiving device, by means of which the handle part 4 is connected by radio to the control and data processing unit 5.

Figure 2:
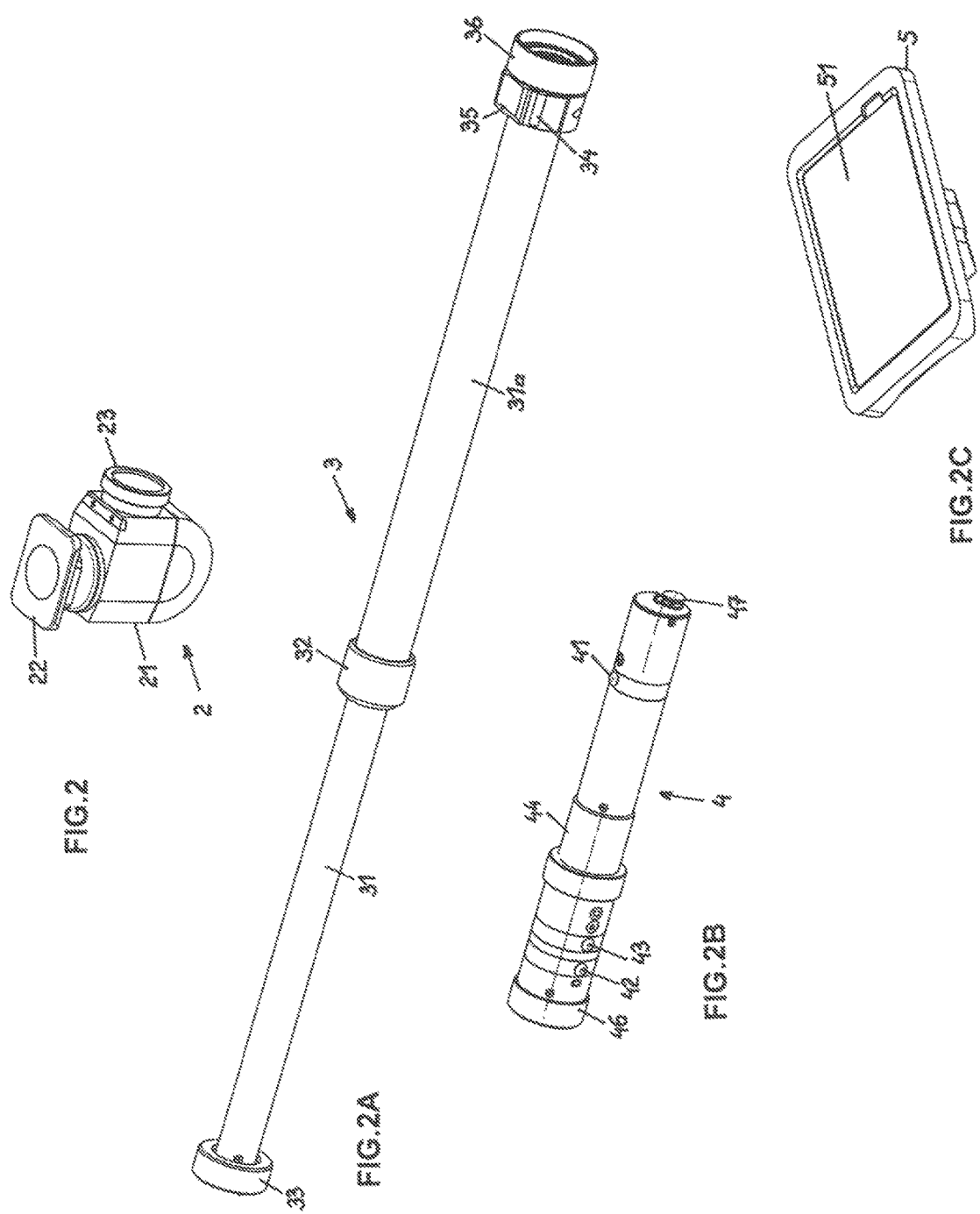

As can be seen from FIG. 2, the measuring device 2 is formed with a housing 21, in which there is a moisture sensor 22, which is pressed against the underside of the wire 11 for the performance of the measurements. Furthermore, the measuring device 2 is provided with a coupling part 23 for its connection to the measuring rod 3.

As can be seen from FIG. 2A, the measuring rod 3 comprises two tubular pieces 31 and 31a, which can be displaced in one another and which can be fixed in their mutual position by means of a clamping ring 32, which means that the length of the measuring rod 3 is adjustable. At its left-hand end, the measuring rod 3 is formed with a first coupling part 33, which is assigned to the coupling part 23 of the measuring device 2. Furthermore, the measuring rod 3 is equipped with a spirit level 34 and with a digital display 35. At its right-hand end, the measuring rod 3 is formed with a second coupling part 36, which is used to connect the measuring rod 3 to the handle part 4.

As can be seen from FIG. 2B, the handle part 4 is formed with an on/off button 41, with a function button 42, with a start button 43 and with a transparent region 44 with an LED lamp. On its left-hand end part, the handle part 4 is formed with a first coupling part 46, which is assigned to the coupling part 36 of the measuring rod 3. On its right-hand end part, the handle part 4 is formed with a charging socket 47. Electric and electronic devices for performing the measurements are located in the interior of the handle part 4, such as a data memory, a transmitting and receiving device, control devices, switching devices and the like, and also a battery.

Illustrated in FIG. 2C is the control and data memory unit 5, which is formed with a display 51 and which is likewise formed with a transmitting and receiving device, which interacts with the transmitting and receiving device located in the handle part 4.

For the performance of measurements, the measuring device 2, the measuring rod 3 and the handle part 4 are connected to one another, as illustrated in FIG. 1, and the means 2 is pressed against the underside of the wire 11.

Figure 3:
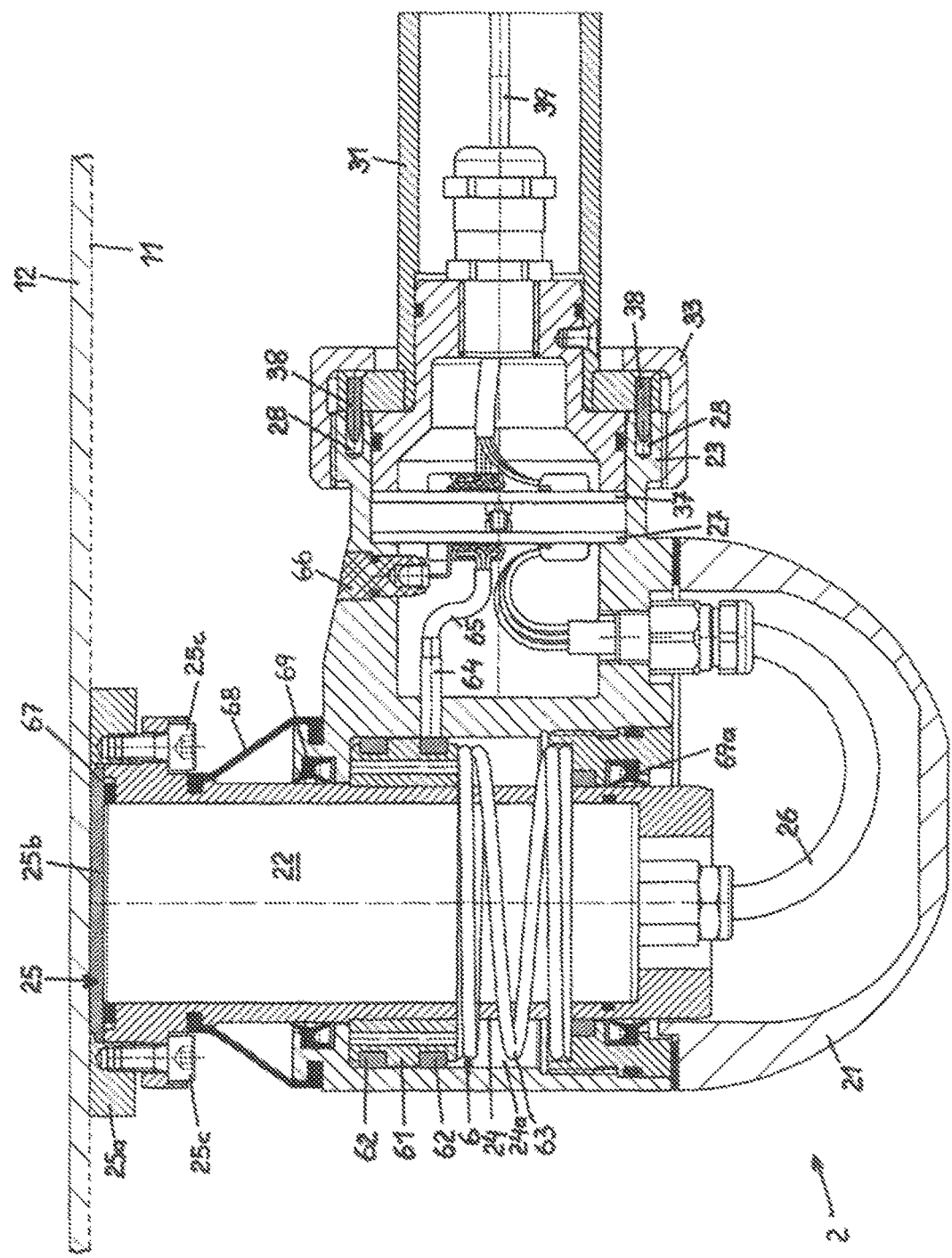
FIG. 3 is a vertical section taken through an apparatus for measuring the moisture content of the pulp material on a wire, which forms a constituent part of the apparatus according to FIG. 1, in a first position of a device for determining the contact pressure.

In FIG. 3, the means 2 for measuring the moisture content of the pulp material 12 on the wire 11 in an installation for paper production is illustrated. The means 2 is formed with the housing 21, which encloses a cylindrical cavity 24. Located in this cavity 24 is the sensor 22 for measuring the moisture content of the pulp material 12. At the upper end of the sensor 22 there is a measuring plate 25, which comprises an outer metallic ring part 25a and an inner part 25b of a ceramic material. The ring part 25a is fixed to the sensor 22 by screws 25c. The inner part 25b is replaceably fixed by means of the ring part 25a to the sensor 22. The construction of the inner part 25b, by which the measurements are influenced, is chosen so as to correspond to specific requirements of the measurements. The output from the sensor 22 is led via a line 26 to a circuit board 27, which is located in the coupling part 23.

To achieve accurate results of the measurements of the moisture content of the pulp material 12, it is necessary to press the measuring device 2 against the wire 11 with a pressure which is in a predefined pressure range. In order to ensure this, the sensor 22 is vertically adjustably mounted within the cavity 24, and the measuring device 2 is formed with a pressure measurement device 6 for achieving a contact pressure within the predefined range. The cavity 24 is formed with a widened portion 24a of annular cross section. Fixed to the sensor 22 is a sliding sleeve 61, which is formed with two sliding rings 62 located at an axial distance from each other. Between the sliding sleeve 61 and the lower end face of the widened portion 24a there is a spring element 63 in the form of a helical compression spring, which acts between the housing 21 and the sensor 22. As soon as the sensor 22 is pressed with the measuring plate 25 against the underside of the wire 11, it is displaced downward counter to the action of the helical compression spring 63 in the housing 21, as a result of which the helical compression spring 63 is compressed; the pressure produced by the latter, with which the sensor 22 is pressed against the wire 11, rises.

The upper end position of the sensor 22, on which the measuring plate 22 rests with only little pressure against the wire 11, is illustrated in FIG. 3. By contrast, in FIG. 3A a central vertical position of the sensor 22 is illustrated, in which a moderate pressure, with which the sensor 22 is pressed against the wire 11, is exerted by the helical compression spring 63.

In order to measure that pressure with which the measuring plate 25 is pressed against the wire 11, and to take said pressure into account in the measured results, the sliding sleeve 61 is assigned a position sensor 64. The sliding sleeve 61 is produced from a metal. By contrast, the sliding rings 62 are produced from a plastic material. During a displacement of the sliding sleeve 61 and the sliding rings 62 with respect to the position sensor 64, on the basis of the change in the electrical conductivity of the region located opposite said sensor, that position in which the position sensor 64 is located between the two sliding rings 62 is measured. In this position, the predefined contact pressure is produced by the helical compression spring 63. The output from the position sensor 64 is led via a line 65 to an LED lamp 66 in the housing 21, by means of which the position of the sensor 22 that is required for the predefined contact pressure is indicated. Since the line 52 is also connected to the circuit board 27, the contact pressure is also transmitted to the control and data processing unit 5.

Between the inner part 25b of the measuring plate 25 and the sensor 22 for measuring the moisture content of the paper pulp 12, there is a sealing ring 67. Furthermore, between the sensor 22 and the housing 21 there is a sealing cuff 68. In addition, the sensor 22 is sealed off with respect to the housing 21 by means of further sealing rings 69 and 69a. By means of the sealing elements 67, 68, 69, 69a, liquid escaping from the pulp material 12 is prevented from penetrating into the housing 21. In this way, the means 6 for producing the intended pressure with which the sensor 22 is pressed against the wire 11 is protected against the ingress of liquid, which means that said sensor is not damaged and remains serviceable.

To couple the means 2 for measuring the moisture content to the measuring rod 3, use is made firstly of the coupling part 23 and secondly of the coupling part 33 of the measuring rod 3. The coupling part 23 is formed as a tubular piece, which is formed with an external thread. The coupling part 33 is formed as a union nut, which is screwed onto the coupling part 23. Within this coupling, the circuit board 27 is assigned a circuit board 37 belonging to the measuring rod 3. These two circuit boards 27 and 37 are formed with contacts assigned to one another. In order to bring the circuit boards 27 and 37 into the correct position on one another in the installation during the coupling of the measuring device 2 and the measuring rod 3, the coupling part 23 is formed with positioning holes 28 and the coupling part 33 is formed with positioning pins 38, which are assigned to the positioning holes 28. A helically formed data line 39, which is located within the measuring rod 3, is connected to the circuit board 37. By means of the spirit level 34 on the measuring rod 3, the angular position of the measuring device 2 with respect to the wire 11 can be checked. Selected data which is relevant to the performance of the measurements is displayed by the display 35.

The entire apparatus 1 for measuring the moisture content of the pulp material 12 on the wire 11 is switched on by the on-off button 41 located in the handle part 4. Selection and setting of functions is carried out via the function button 42. By means of the start button 43, as soon as the necessary contact pressure of the sensor 22 on the wire 11 is reached, which is indicated by means of the position sensor 64 by the LED lamp 66, the measurements of the moisture content of the pulp material 12 on the wire 11 are performed. All the data relating to the positioning of the measuring device 2 and the results of the measurements is stored in a buffer memory located in the handle part 4. Furthermore, this data is transmitted via the transmitting device located in the handle part 4 to the control and data processing unit 5, in which said data is stored and evaluated; said data can be displayed on the display 51.

The apparatus is put into use as follows:

The constructional features of an installation for paper production are loaded in the control and data processing unit 5 and the installation is displayed on the display 51. Furthermore, the critical data for the operation of the installation, such as the speed at which the wire 11 is moved, and the parameters of the paper which is produced, are stored in the control and data processing system 5. Next, those points at which measurements of the moisture content are to be performed are stored, these measuring points likewise being displayed on the display 51. Furthermore, a measurement program is input which, amongst other things, consists in whether a calibration is performed before the start of the measurements. Hereupon, the measuring device 2 is pressed against the wire 11 at the individual measuring points. As soon as that pressure with which the measuring device 2 is pressed against the wire 11 is in the predefined range, the measurements of the moisture content of the pulp material 12 are performed. The measured values obtained as a result are assigned to the individual measuring points and stored. The measured results are then evaluated and are used for the control of the production process.

The invention claimed is:

1. A method for measuring a moisture content of pulp material on a wire in an installation for producing paper, the method comprising:
    providing a measuring device for measuring the moisture content of the pulp material and a control and data processing unit configured to receive measured data from the measuring device;
    measuring the moisture content of the pulp material with the measuring device and concomitantly pressing the measuring device onto an underside of the wire with a given contact pressure; and
    determining the contact pressure with which the measuring device is pressed onto the underside of the wire and measuring the moisture content while maintaining the contact pressure within a predefined range.

2. An apparatus for measuring the moisture content of pulp material on a wire in an installation for producing paper, the apparatus comprising:
    a measuring device for measuring the moisture content of the pulp material and acquiring measured data, said measuring device including a moisture sensor and an optional attachment member for affixing to a measuring rod;
a control and data processing unit;
a transmitting and receiving device and/or a connection terminal for a data line for transmitting the measured data to said control and data processing unit; and
said measuring device including a pressure measurement device for determining and displaying a pressure range with which said measuring device is pressed against the wire.

3. The apparatus according to claim 2, wherein the measuring device for measuring the moisture content is formed with a housing, and said moisture sensor is displaceably mounted in said housing, subject to a spring element.

4. The apparatus according to claim 3, wherein said housing is formed with a cylindrical cavity, said moisture sensor is disposed in said cylindrical cavity, and said moisture sensor is displaceable within said cavity under an action of said spring element.

5. The apparatus according to claim 4, wherein the spring element is a helical compression spring disposed to act between said moisture sensor and said housing.

6. The apparatus according to claim 4, wherein said cylindrical cavity in said housing is formed with a region of annular cross section and said moisture sensor is formed with a sliding sleeve affixed thereto and disposed to project into said annular region and to be displaced between its end faces.

7. The apparatus according to claim 6, wherein said spring element is located between said sliding sleeve and said housing.

8. The apparatus according to claim 2, wherein said moisture sensor is formed with a wear-resistant support on a side thereof facing the wire.

9. The apparatus according to claim 8, wherein said wear-resistant support is a plate of a ceramic material.

10. The apparatus according to claim 8, wherein said wear-resistant support is replaceably fixed to said moisture sensor.

11. The apparatus according to claim 10, which comprises a seal disposed between said support of ceramic material and said moisture sensor.

12. The apparatus according to claim 3, which comprises a resilient sealing cuff disposed to seal said moisture sensor and said housing with respect to an entry of liquid.

13. The apparatus according to claim 12, which further comprises at least one sealing ring.

14. The apparatus according to claim 6, wherein said sliding sleeve is assigned at least one position sensor configured to determine and display a position of said moisture sensor with respect to said housing.

15. The apparatus according to claim 14, wherein said sliding sleeve is formed with two sliding rings located at an axial spacing distance from each other and configured to interact with said position sensor.

16. The apparatus according to claim 15, which comprises an LED lamp located in said housing and connected to said position sensor, said LED lamp outputting a light signal as soon as said position sensor is located in a region between said sliding rings as a result of a displacement of said moisture sensor with respect to the housing.

17. The apparatus according to claim 3, wherein said housing of said measuring device and said measuring rod are formed with coupling parts assigned to one another for mechanical and electrical connection.

18. The apparatus according to claim 17, wherein said coupling parts are formed with circuit boards assigned to each other and centering elements.

19. The apparatus according to claim 17, wherein a length of said measuring rod is adjustable and fixable.

* * * * *